United States Patent
Liang

(10) Patent No.: US 10,335,487 B2
(45) Date of Patent: Jul. 2, 2019

(54) METHODS FOR TARGETING OR STIMULATING CELLS OR ORGANISMS USING NANOPARTICLES AND EXTERNAL FIELD

(71) Applicant: Ping Liang, Newport Coast, CA (US)

(72) Inventor: Ping Liang, Newport Coast, CA (US)

(73) Assignee: Ping Liang, Newport Coast, CA (US)

( * ) Notice: Subject to any disclaimer, the term of this patent is extended or adjusted under 35 U.S.C. 154(b) by 0 days.

(21) Appl. No.: 15/578,218

(22) PCT Filed: Jun. 15, 2016

(86) PCT No.: PCT/US2016/037619
§ 371 (c)(1),
(2) Date: Nov. 29, 2017

(87) PCT Pub. No.: WO2016/205363
PCT Pub. Date: Dec. 22, 2016

(65) Prior Publication Data
US 2018/0153992 A1  Jun. 7, 2018

Related U.S. Application Data

(60) Provisional application No. 62/181,936, filed on Jun. 19, 2015.

(51) Int. Cl.
*A61K 9/00* (2006.01)
*A61N 2/02* (2006.01)
(Continued)

(52) U.S. Cl.
CPC ............ *A61K 41/00* (2013.01); *A61K 9/0009* (2013.01); *A61K 9/0014* (2013.01); *A61K 9/0019* (2013.01); *A61K 9/143* (2013.01); *A61K 9/5115* (2013.01); *A61M 37/00* (2013.01); *A61N 1/325* (2013.01); *A61N 1/40* (2013.01); *A61N 2/002* (2013.01); *A61N 2/02* (2013.01);
(Continued)

(58) Field of Classification Search
CPC . A61N 2/00–2/12; B82Y 5/00; H01F 1/0045; H01F 1/0054; A61K 9/0009; A61K 9/0019
See application file for complete search history.

(56) References Cited

U.S. PATENT DOCUMENTS

2009/0226521 A1* 9/2009 Smyth ................. A61K 9/0009
424/484

FOREIGN PATENT DOCUMENTS

WO 2003022360 A2 3/2003
WO 2014074584 A1 5/2014

OTHER PUBLICATIONS

Kavanagh et al. "Use of a neuromuscular electrical stimulation device for facial muscle toning: a randomized, controlled trial", J Cosmet Dermatol, Dec. 2012, vol. 11, pp. 261-266.
(Continued)

*Primary Examiner* — Thaddeus B Cox
(74) *Attorney, Agent, or Firm* — Guosheng Wang; United States Research and Patent Firm

(57) ABSTRACT

This invention presents methods for targeting and killing types of cells or organisms using Magneto-Electric Nano-Particles under the control of an external magnetic field. A method was also presented for using Magneto-Electric Nano-Particles to stimulate or rejuvenate cells under an external magnetic field.

8 Claims, 3 Drawing Sheets

(51) Int. Cl.

| | | |
|---|---|---|
| *A61N 2/06* | (2006.01) | |
| *H01F 1/00* | (2006.01) | |
| *B82Y 25/00* | (2011.01) | |
| *A61K 41/00* | (2006.01) | |
| *A61K 9/14* | (2006.01) | |
| *A61M 37/00* | (2006.01) | |
| *A61N 1/40* | (2006.01) | |
| *A61K 9/51* | (2006.01) | |
| *A61N 1/32* | (2006.01) | |
| *A61N 2/00* | (2006.01) | |
| *B82Y 30/00* | (2011.01) | |

(52) U.S. Cl.
CPC ............. *A61N 2/06* (2013.01); *H01F 1/0054* (2013.01); *B82Y 25/00* (2013.01); *B82Y 30/00* (2013.01)

(56) References Cited

OTHER PUBLICATIONS

Yue et al. "Magneto-electric nano-particles for non-invasive brain stimulation", PLoS One, Sep. 5, 2012, vol. 7, e44040, pp. 1-5.

Guduru et al. "Magneto-electric nano-particles to enable field-controlled high-specificity drug delivery to eradicate ovarian cancer cells", Sci Rep, Oct. 16, 2013, vol. 3:2953, pp. 1-8.

Kaushik et al. "The potential of magneto-electric nanocamers for drug delivery", Expert Opin Drug Deliv, Jul. 2, 2014, vol. 11, pp. 1-20 [Original pp. 1635-1646].

Nair et al. "Externally controlled on-demand release of anti-HIV drug using magneto-electric nano-particles as carriers", Nat Commun, Apr. 16, 2013, vol. 4:1707, pp. 1-7.

Search Report and Written Opinion of the ISA, PCT/US16/37619, WO 2016/205363, dated Sep. 6, 2016.

* cited by examiner

METHODS FOR TARGETING OR STIMULATING CELLS OR ORGANISMS USING NANOPARTICLES AND EXTERNAL FIELD

This application claims the benefit of U.S. Provisional Application No. 62/181,936 filed on Jun. 19, 2015.

FIELD OF INVENTION

The present invention relates to a method for targeting or stimulating types of cells or organisms using nanoparticles and an external field, and more specifically, using Magneto-Electric Nano-Particles (MENPs) and an external magnetic field.

BACKGROUND

An important step in killing cancer cells is to bring and accumulate cancer killing agents to sites containing cancer cells, or more preferably, bring them to the membrane of cancer cells. A type of such cancer killing agents is various nano-particles possessing certain properties or carrying cancer-killing drugs. An effective method to achieve this purpose is to coat the nano-particles with ligands or antibodies that only binds to the membrane of the cancer cells to be targeted. This method depends on the availability of ligands or antibodies matching the cancer cells to be targeted. There is also an Enhanced Permeability and Retention (EPR) effect that preferably accumulates nano-particles at a cancer site than normal cells because of the increased blood flow to a cancer site. However, the EPR may not accumulate enough nano-particles to reach the amount and density needed for treatment.

It is known that cell functions and growth can be affected by electric signals. One desired effect is the stimulation or rejuvenation of skin cells for a firmer or more youthful appearance. S. Kavanagh et al. ("Use of a neuromuscular electrical stimulation device for facial muscle toning: a randomized, controlled trial", Journal of Cosmetic Dermatology, 2012 December; 11(4):261-6. doi: 10.1111/jocd.12007) showed that in a 12-week trial, facial neuromuscular electrical stimulation (MMES) was associated with increased thickness of the zygomatic major muscle and subjective improvements in facial attributes. Such LAMES devices use point contact electrodes to apply the electric stimulation, as a result, uniform stimulation at cellular levels cannot be achieved. Also, EPR strongly depends on the nano-particles' size and thus is limited to relatively large nano-particles.

There is an urgent need for killing viruses and antibiotic-resistant bacteria and a method that is effective and applicable to a large variety of viruses and bacteria is lacking.

There is no prior art that possess the functions of the embodiments presented in this application.

DESCRIPTION OF EMBODIMENTS

Reference may now be made to the drawings wherein like numerals refer to like parts throughout. Exemplary embodiments of the invention may now be described. The exemplary embodiments are provided to illustrate aspects of the invention and should not be construed as limiting the scope of the invention. When the exemplary embodiments are described with reference to block diagrams or flowcharts, each block represents both a method step and an apparatus element for performing the method step.

Method for Targeting a Type of Cells Using Nanoparticles and External Field

It is an established fact that cell membrane exhibits a negative charge, and moreover, the membrane of cancer cells stores a significantly less negative charge than normal cells, as much as an order of magnitude less negative surface charge compared to normal cells. Therefore, if nano-particles also exhibit negative charge, the electric field gradient force established by these charges will push the nano-particles towards cancer cells. The stronger the negative charges on the nano-particles, the stronger the force that will push the nano-particles to cancer cells, thus achieving the objective of targeting cancer cells while avoiding normal cells.

Figure 1:
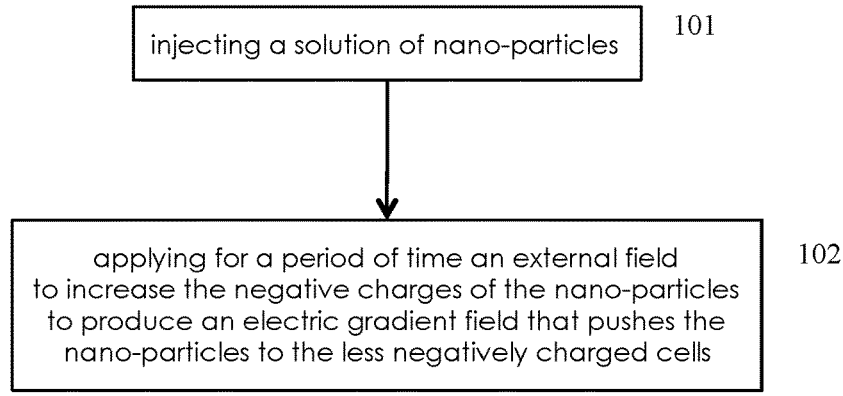
FIG. 1 shows an embodiment for targeting cells that are less negatively charged than surrounding cells.

One embodiment is a method for targeting cells that are less negatively charged than surrounding cells, e.g., targeting cancer cells which are less negatively charged than normal cells, comprising injecting a solution of nano-particles 101; applying for a period of time an external field that will increase the negative charges of the nano-particles so as to produce an electric gradient field that pushes the nano-particles to the less negatively charged cells 102, see FIG. 1.

One type of nano-particles that can be used in this embodiment is Magneto-Electric Nano-Particles (MENPs) and the external field is a magnetic field. When a magnetic field is applied to MENPs, the particles produce an electric polarization due to the magnetic-electric coupling property of the particles. This electric polarization increases the negative charges of the MENPs. The increased negative charges on the MENPs and the more negatively charged normal cells create a non-zero electric-field gradient that pushes the MENPs away from the normal cells and moving towards the less negatively charged cancer cells, effectively increasing specificity of the targeting of the cancer cells by the MENPs.

Figure 2:
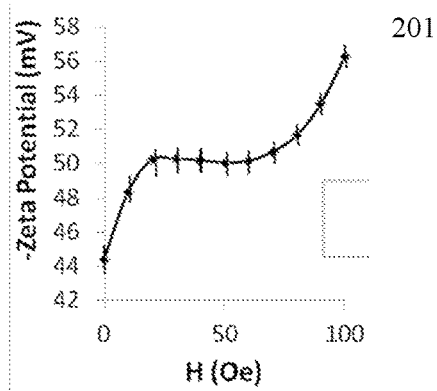
FIG. 2 shows measurement of Zeta Potential of MENPs as a function of magnetic field in blood or other body fluid.

One type of MENPs is made with a basic structure of $CoFe_2O_4$—$BaTiO_3$ coreshell. One embodiment uses 30-nm MENPs synthesized from the following steps: 1) 0.058 g of $Co(NO_3)_2 \cdot 6H_2O$ and 0.16 g of $Fe(NO_3)_3 \cdot 9H_2O$ are dissolved in 15 mL of deionized (DI) water; 2) 5 mL of aqueous solution containing 0.9 g of sodium borohydride and 0.2 g of polyvinylpyrrolidone is added at 120° C. for 12 hours to obtain $CoFe_2O_4$ nanoparticles; 3) $BaTiO_3$ precursor solution is prepared by adding 30 mL of DI water containing 0.029 g of $BaCO_3$ and 0.1 g of citric acid to 30 mL ethanolic solution containing 1 g of citric acid and 0.048 mL of titanium (IV) isopropoxide; 4) As-prepared $CoFe_2O_4$ nanoparticles (0.1 g) is added to the 60 mL of $BaTiO_3$ precursor solution and sonicated for 120 min; 5) The resulted dispersed nanoparticles is dried on hot plate at 60° C. for 12 hours, while stirring at 200 rpm; 6) The obtained powder is heated at 780° C. for 5 hour in a box-furnace and cooled at 52° C. min$^{-1}$ to obtain 30 nm-sized $CoFe_2O_4$—$BaTiO_3$ coreshell MENPs. In another embodiment, the nano-particles are further surface functionalized by a compound, e.g., a 2-nm thick coating of glycerol mono-oleate (GMO) using the following steps: (i) GMO-MENPs is prepared by incubating 0.1 mg of GMO with 5 mg of MENPs in 5 mL of PBS (pH 7.4) buffer for 12 hours; to achieve uniform surface modification, the solution is slowly agitated during incubation; (ii) The solution is centrifuged at 20000 rpm for 20 min at 10° C. to remove excess GMO; (iii) The obtained pellet is re-suspended in ethyl acetate:acetone (70:30) solution and re-centrifuged three times to obtain GMO-MENPs. (iv) Surface-modified MENPs were lyophilized and stored at 4° C. until further use. The particle size distribution can be measured by a Zetasizer Nano series that uses the standard dynamic light scattering (DLS) approach. The measured Zeta Potentials were −45+/−1.72 mV for non-functionalized MENPs and −41.6+/−0.26 mV for functionalized (with GMO) MENPs. When magnetic field is applied to the MENPs, the Zeta Potential can change to approximately −50 mV and −57 mV at approximately 25 Oe and 100 Oe respectively, see 201 in FIG. 2.

Since the electric gradient field force is effective on the MENPs when the nano-particles are in the close proximity of the less negatively charged cells, one embodiment further comprises using an external field to guide and/or enhance the accumulation of the nano-particles into a site containing the less negatively charged cells than the surrounding more negatively charged cells. In one case, one or more permanent magnets or electro-magnets can be placed, injected or implanted in or near a cancer site, whereas the magnet(s) serves to attract MENPs to and increase accumulation of MENPs in the cancer site, as well as to increase the negative charges of the MENPs to steer the MENPs towards the cancer cells.

Wires, liquid capsules, injectable macro-particles (i.e., particles that are larger than the nano-particles described above) or other injectable or implantable forms, made of permanent magnetic material can be injected into solid tumor site that are deep inside the body or an organ. The magnetic field produced by these sources serve to localize and accumulate the MENPs at cancer sites, and at the same time to enhance the electric field gradient to push MENPs to the cancer cells.

In another embodiment, a changing magnetic field is used instead of a constant one to generate a varying or pulsating force to push MENPs towards less negatively charged cells. The changing magnetic field can be generated by driving a periodic or irregular alternating current through one or more electro-magnets, e.g., a sine or square wave current, or by varying the position of one or more permanent magnets, e.g., rolling, rotating or moving back and forth of permanent magnets. The period, pattern, magnitude and/or direction of the alternating magnetic field can be changed to achieve desired movements of the MENPs.

One advantage of using MENPs in the above embodiments is that the increase of negative charge can be controlled externally using a magnetic field, either using a constant magnetic field to cause a constant increase of negative charge on the MENPs, or using an alternating magnetic field of a chosen pattern to cause a pulsating change of the negative charge on the MENPs. Another advantage is that magnetic field can be used to increase the accumulation MENPs at a targeted site and/or prevent the spreading MENPs from a targeted site. In applications where these two advantages are not important, one embodiment for targeting cells that are less negatively charged than surrounding cells comprises injecting a solution of nano-particles that possess high levels of negative charge without requiring an external field. Higher negative charges on nano-particles can be obtained by changing the chemical composition of the nano-particles or coat or conjugate nano-particles with molecules that increase the negative charge of the nano-particles when they are in a blood stream or body fluid. When the nano-particles that possess high levels of negative charge are in close proximity of the less negatively charged cancer cells, the interaction of the nano-particles and the more negatively charged normal cells create an electric force gradient field that drives the MENPs towards the cancer cells.

Constant (DC) magnetic field and changing (AC) magnetic field play different roles in the embodiments using MENPs for target and killing cancer cells. In cases where both a DC magnetic field and an AC magnetic field are desired at the same time, one embodiment is an apparatus formed into a shape and dimension to fit a target area or volume that is made of or using permanent magnetic material and with one or more, e.g., an array of, electromagnets embedded in the apparatus to generate a DC magnetic field and AC magnetic field simultaneously.

Figure 3:
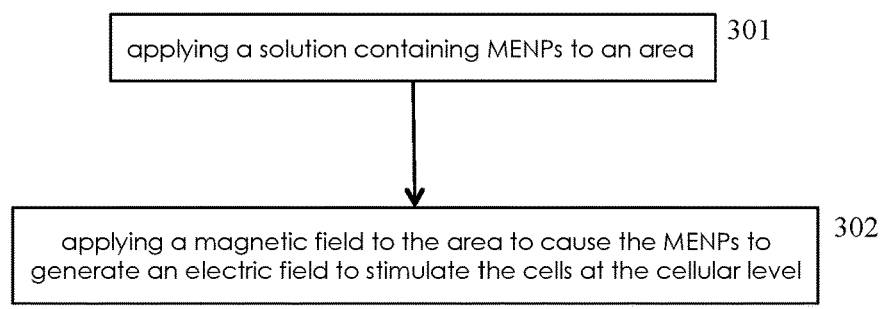
FIG. 3 shows the components and attachments of another embodiment imaging head.

Method for Skin or Neuromuscular Electrical Stimulation at Cellular Level Using MENPs and Magnetic Field One embodiment is a method for skin and appearance improvement comprising applying a solution containing MENPs to an area 301, whereas applying can be topically spreading on a skin area in the same fashion as skin moisturizer, applying into deeper skin layer using microabrasion, microdermabrasion, micropuncture using superfine needs, subcutaneous injection or other methods that can spread the MENP solution into deeper skin layers or muscles; and applying a magnetic field to the area for a period of time to cause the MENPs to generate an electric field to stimulate the cells 302. Because the electric field is local to each MENP and the MENPs are spread out in the area, the embodiment achieves electric stimulation at cellular level, as shown in FIG. 3.

In one embodiment, a changing (AC) magnetic field is applied to generate changing electric field on the MENPs to deliver pulsating electric stimulations to the cells near, attached to or surrounding the MENPs. The frequency, magnitude and/or direction of the alternating current driving one or more electromagnets to generate the AC magnetic field can be adjusted to achieve a desired electric stimulation effect.

When it is desired to keep the MENPs within a local area where it is applied, a magnetic field, preferably a constant (DC) magnetic field using one or more permanent magnets or electromagnets driven by direct current, is applied immediately after the MENP solution is applied or simultaneously while the MENP solution is being applied. One way to apply a magnetic field to keep the MENPs to the area or close to the surface to where the solution is applied is to use a magnetic applicator, e.g., a patch or mold made with permanent magnetic material that is applied immediately after the MENP solution is applied or simultaneously while the MENP solution is being applied. In another embodiment, the DC magnetic field provides a bias to keep the MENPs to the area or close to the surface to where the solution is applied, and a changing (AC) magnetic field is additionally applied to generate a changing electric field on the MENPs to deliver pulsating electric stimulations to the cells near, attached to or surrounding the MENPs.

One application of the above embodiments is for a treatment to firm or tone facial or neck appearance. To apply the magnetic field evenly for even electric stimulation and effect, one embodiment uses a flexible facial mask or facial mold made with permanent magnetic material and/or embedded with an array of electromagnets, to generate an evenly distributed DC magnetic field, or AC magnetic field, or a DC magnetic field and AC magnetic field simultaneously.

The above embodiment can be generalized for deep muscle or tissue toning by injecting the MENPs into the muscle or tissue and apply magnetic field to the area or volume. Thus, one embodiment is a method for muscle or tissue toning comprising injecting a solution containing MENPs to a muscle or tissue area or volume; and applying a magnetic field to the area or volume to cause the MENPs to generate an electric field to stimulate the cells of the muscle or tissue.

When it is desired to prevent MENPs from spreading to other parts of the body, MENPs can be coated or conjugated with targeting agents, e.g., molecules or proteins, that bind to the cells to be stimulated, e.g., bind to skin cells or muscle cells.

When it is desired to remove the MENPs from the body, an apparatus, e.g., mask, mold or roller, that have a sufficiently strong magnetic field can be applied to the areas with MENPs to attract the MENPs to the apparatus, thus removing them from the body. Another embodiment uses an extraction solution that contains agents that binds to the MENPs and can attract the MENPs to the surface and wash them off together with the extraction solution.

Method for Killing Viruses and Antibiotic-Resistance Bacteria Using MENPs and Magnetic Field In this application, an antibody can mean immunoglobulin, antibody mimetic, ligands, or other molecules or proteins that bind to a targeted bacterium or virus.

Figure 4:
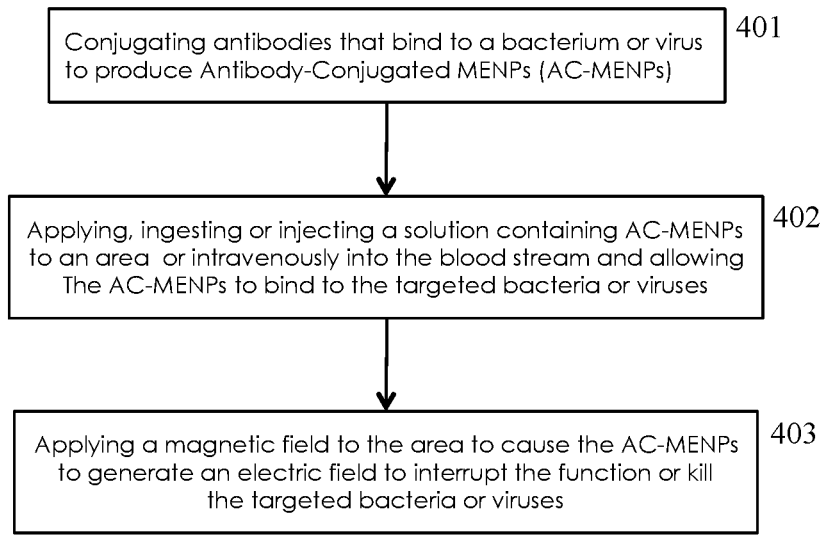
FIG. 4 shows a method for killing bacteria or viruses using AC-MENPs.

One embodiment is a method for killing bacteria or viruses comprising coating, binding or conjugating antibodies that bind to a bacterium or virus to MENPs to produce Antibody-Conjugated MENPs (AC-MENPs) 401; applying, ingesting or injecting a solution containing AC-MENPs to an area or intravenously into the blood stream and allowing the AC-MENPs to bind to the targeted bacteria or viruses 402; and applying a magnetic field to the area to cause the AC-MENPs to generate an electric field to interrupt the function or kill the targeted bacteria or viruses 403, as shown in FIG. 4. The magnetic field can be constant as produced by one or more permanent magnets, or changing as produced by electromagnets driven by varying electric currents under the control of a microcontroller or other analog or digital control circuits.

Furthermore, the characteristics of the magnetic field, e.g., frequency, pattern, magnitude and direction, can be adjusted to generate an electric field sufficient to interrupt the function or kill the targeted bacteria or viruses. At the same time, the characteristics of the magnetic field may be chosen to avoid or minimize damages to surrounding normal cells.

One embodiment of MENPs is $CoFe_2O_4$—$BaTiO_3$ coreshell which can be prepared as in Corral-Flores et. al. (Corral-Flores, V. Bueno-Baques, D. & Ziolo, R. Synthesis and characterization of novel $CoFe_2O_4$—$BaTiO_3$ multiferroic core-shell-type nanostructures. *Acta Mater.* 58, 764-769, 2010). In this procedure, $CoFe_2O_4$ particles are first prepared by the standard hydrothermal method, with 0.058 g of $Co(NO_3)_2.6H_2O$ and 0.16 g of $Fe(NO_3)_3.9H_2O$ dissolved in 15 ml of distill water and 0.2 g of polyvinylpyrrolidone dissolved in S ml of aqueous solution containing 0.9 g of sodium borohydride at 120° C. for 12 hours. Then, precursor solution of $BaTiO_3$ is prepared by mixing 30 ml of aqueous solution containing 0.029 g of $BaCO_3$ and 0.1 g of citric acid with 30 ml of ethanolic solution containing 1 g of citric acid and 0.048 ml of titanium (IV) isopropoxide. Coreshell $CoFe_2O_4$—$BaTiO_3$ MENPs are prepared by mixing 0.1 g of $CoFe_2O_4$ nanoparticles in the $BaTiO_3$ precursor solution and the mixture is sonicated for 2 hours. Once the $CoFe_2O_4$ nanoparticles are thoroughly dispersed, the mixture is dried on the hot plate at 60° C. overnight while continuously stirring. The dried powder is subjected to 780° C. for 5 hours in a furnace (CMF-1100) and cooled at 52° C. per minute to obtained the coreshell MENPs of ~30 nm diameter.

In another embodiment, the MENPs' surface is coated with a layer of compound, e.g., glycerol monooleate (GMO). The GMO layer can be coated by adding 1 mg of GMO to 5 mg of MENPs in 5 ml of the PBS buffer. The mixture is then incubated for 12 hours while being slowly rotated in order to achieve uniform coating. Upon completion of the incubation process, the nanoparticles are centrifuged at 20,000 rpm for 20 minutes at 10° C. The pellet is washed in ethyl acetate:acetone (70:30) solution and re-centrifuged. The washing process is repeated thrice to completely remove the excess unbound GMO. Finally, the obtained pellet is lyophilized for 48 hours and stored for further use.

In one embodiment, antibodies are conjugated to the compound-coated MENPs, e.g., GMO-MENPs, e.g., covalently attaching antibodies onto the compound-coated MENPs' or GMO-MENPs' surface, e.g., following the protocol described by Kocbek et al (Kocbek, P., Obermajer, N., Cegnar, M., Kos, J. & Kristl, J. Targeting cancer cells using PLGA nanoparticles surface modified with monoclonal antibody. J. Controlled Release 120, 18-26, 2007). In one example, to covalently attach antibodies to compound-coated MENPs, the nanoparticle surface is preliminarily functionalized. In the case of GMO-MENPs, 1 mg of GMO-MENPs are added to 500 μl of the PBS buffer (pH 7.4). To this solution, 25 μl of N-(3-Dimethylaminopropyl)-N'-ethyl-carbodiimide hydrochloride (EDC) and 25 μl of N-hydroxysuccinimide (NHS), at 1 mg/ml concentration in the PBS buffer (pH 7.4) are added. The solution is incubated for 4 hours at room temperature while being stirred slowly. Then, the sample is centrifuged at 14,000 rpm for 10 minutes at 10° C. and the pellet is washed three times with 1 ml of the PBS buffer (pH 7.4). To bind antibodies to the functionalized MENPs, 10 μl of the antibodies (1 mg/ml) is added to the pellet along with 300 μl of the PBS buffer (pH 7.4). The solution is incubated for 2 hours while being rotated slowly and kept further at 4° C. overnight. The solution is centrifuged at 14,000 rpm for 10 minutes at 10° C. The pellet s washed thrice with 1 ml of the PBS buffer (pH 7.4) to remove any excess antibody.

In one embodiment, after the AC-MENPs have bound to or have electroporated inside the targeted bacteria or virus, one or more of the following mechanisms is applied to kill the bacteria or virus, (A). Apply an external magnetic field to generate strong enough electric field on the AC-MENPs to kill the bacteria or virus, e.g., local electric fields of >1000 V/cm, which can be attained a few nanometers away from AC-MENPs via the application of an external magnetic field of >100 Oe;

(B). Apply an alternating external magnetic field to induce an alternating electric field on the AC-MENPs whereas the strength and frequency of the field is selected such that it disrupts the functions of the bacteria or viruses, thus causes them to die off;

(C). Apply an alternating external magnetic field to generate heat on the AC-MENPs to kill the bacteria or viruses whereas the strength and frequency of the field is selected to generate sufficient heat to kill the bacteria or viruses without harming surrounding cells or tissues;

(D). Apply an alternating external magnetic field to induce mechanical motions of the AC-MENPs to disrupt the functions or to physically damage the bacteria or viruses, causing them to die off; where the mechanical motions may include linear motion, slicing, collisions or vibrations, or combinations thereof.

In another embodiment, a ferromagnetic resonance strongly dependent on the interaction of AC-MENPs with its nano-environment (in the proximity of a few nanometers away from the nano-particles) is used to selectively disrupt or shut down the operation of the bacteria or viruses, when AC-MENPs are bound to or have electroporated the bacteria or viruses. The ferromagnetic resonance of AC-MENPs depends on the saturation magnetization, which in turn, because of the magneto-electric (ME) effect, strongly depends on the electric fields that are associated with the interaction of AC-MENPs with the nano-environment. As the nano-environment changes, so does the saturation magnetization and consequently the ferromagnetic resonance frequency(ies). This resonant frequency or set of resonant frequencies can be varied in a wide range by varying intrinsic properties, e.g. the magneto-crystalline anisotropy energy and the exchange coupling constant, or extrinsic properties, e.g. the shape-induced anisotropy energy. In addition, the resonant frequency(ies) can be controlled by application of an external DC magnetic field. By specifically selecting the resonant frequencies, certain functions of cancer cells can be shut down with a relatively high specificity on demand. For example, the microtubules responsible for cancer cell proliferation could be remotely controlled via ferromagnetic resonance of the AC-MENPs. Namely, the resonant frequency of AC-MENPs in the proximity (of 2 nm) of the microtubules changes because of the changes in the saturation magnetization. The saturation magnetization change is due to the ME effect caused by the interaction of the AC-MENPs and the microtubules. An external AC magnetic field at the new modified resonant frequency can then by applied to disrupt or cause damages to the bacteria or viruses.

Figure 5:
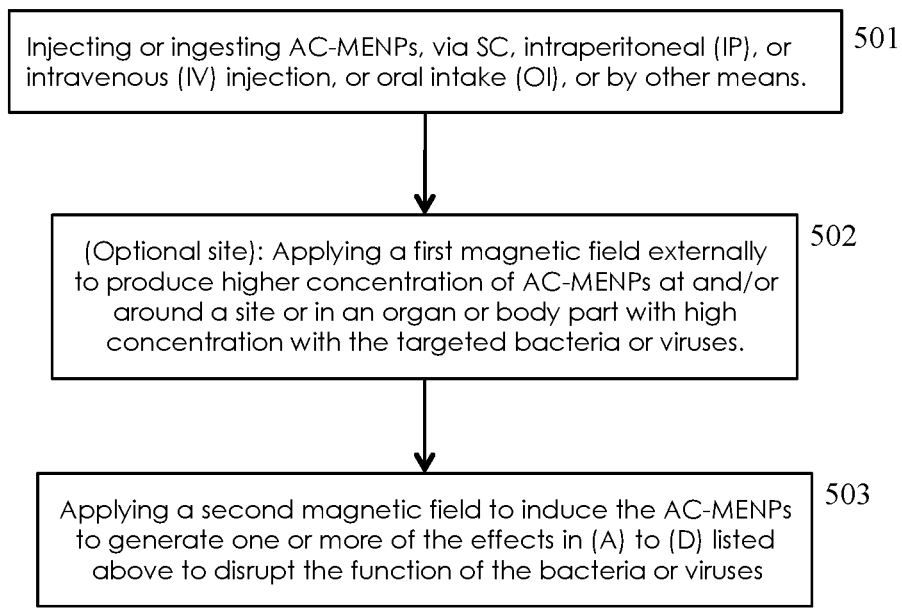
FIG. 5 shows a method for killing targeted bacteria or viruses after the AC-MENPs have bound to or have electroporated inside the targeted bacteria or viruses.

The above mechanisms of targeted killing of bacteria or viruses using AC-MENPs provide a new treatment that is non-toxic or low-toxic. The steps of a preferred embodiment, as shown in FIG. 5, comprise:

Step 1 (501): Injecting or ingesting AC-MENPs, via subcutaneous (SC), intraperitoneal (IP), or intravenous (IV) injection (including IV injection or dripping using a catheter), or oral intake (OD, or by other means.

Step 2 (optional, 502): Applying a first magnetic field externally to produce higher concentration of AC-MENPs at and around a site or in an organ or body part with high concentration with the targeted bacteria or viruses. This step is optional and applicable to a disease site this is localized, e.g., the site of infection or attack by the bacteria or viruses, and is skipped and not or less applicable when the bacteria or viruses are widely distributed, e.g., in the circulatory system).

Step 3 (503): Applying a second magnetic field to induce the AC-MENPs to generate one or more of the effects in (A) to (D) listed above to disrupt the function of the bacteria or viruses.

For a bacteria or virus infection that is localized, a localized second magnetic field this is confined to the disease site is applied. For a disease in which the targeted bacteria or viruses are widely distributed, a wide-area second magnetic field that covers a large body area or the whole or most part of the body is applied so that bacteria or viruses that are circulating in the body can be killed.

In one embodiment, the strength and/or frequency of the second magnetic field in Step 3 is chosen to cause the AC-MENPs to kill targeted bacteria or viruses but does not cause other AC-MENPs that still remain in the body and unbound to targeted bacteria or viruses to harm healthy or untargeted cells. In another embodiment, a sufficiently long waiting period is inserted between Steps 1 and 3 to give the body sufficient time to excrete most or all of the free AC-MENPs that did not bind to bacteria or viruses out of the body. This reduces the risk of AC-MENPs killing healthy or untargeted cells and gives more freedom in selecting the strength and/or frequency of the second magnetic field in Step 3 to kill the bacteria or virus.

Shape, size, ME coupling and other properties are important for the embodiments of this invention. One embodiment for making AC-MENPs with a wide range of properties comprises first depositing a thin film with the required properties via sputter deposition, evaporation, or another deposition technique, and then using ion beam proximity lithography (IBL) or imprint or another advanced lithography method to "cut" the thin films into AC-MENPs of desired shapes and sizes.

In addition to cure diseases caused by bacteria and viruses, the above embodiments can also be used for skin peeling to reveal a more youthful new skin. In one embodiment, a solution of MENPs coated, bound or conjugated with proteins or molecules that bind to skin cells are applied to the a skin area, e.g., face, a strong magnetic field is applied to produce electric field that kills the cells in a surface layer of the skin. The dead layer will then peel off, and a new layer of more youthful looking skin cells grow.

Figure 6:
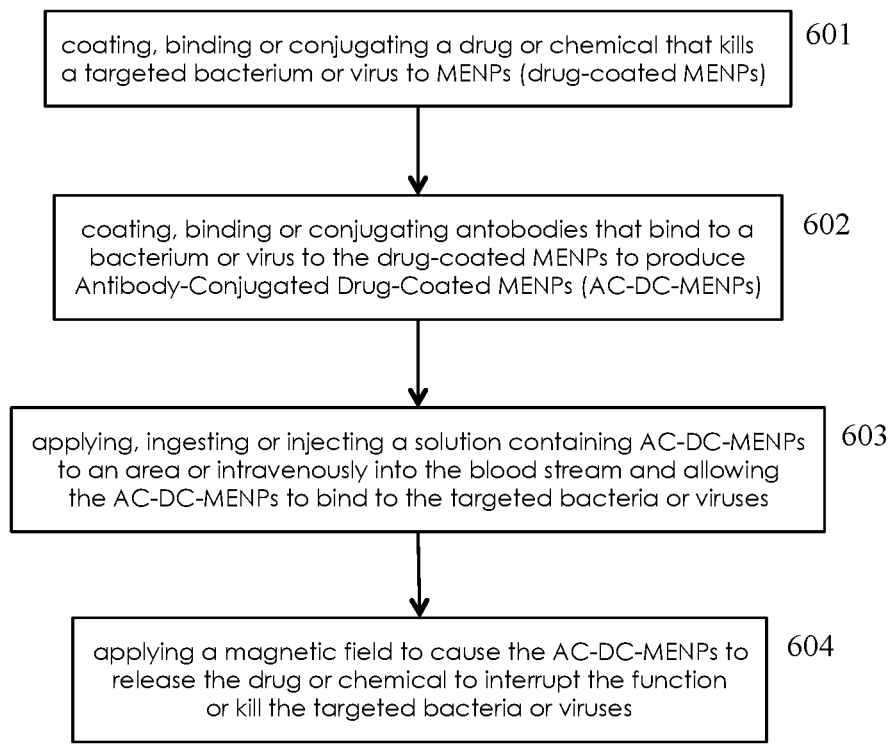
FIG. 6 shows a method for using AC-MENPs to deliver chemicals or drugs to killing bacteria or viruses.

It is known that drugs or chemicals coated, bound or conjugated to MENPs can be released by applying an external magnetic field, as shown by Nair et. al (M Nair, R Guduru, P Liang, J Hong, V Sagar and S Khizroev, "Externally controlled on-demand release of anti-HIV drug using magneto-electric nanoparticles as carriers", Nature Communications 4, Article number: 1707, 2013). Another embodiment is a method for killing bacteria or viruses comprising coating, binding or conjugating a drug or chemical that kills a targeted bacterium or virus to MENPs (drug-coated MENPs) 601; coating, binding or conjugating antibodies that bind to a bacterium or virus to the drug-coated MENPs to produce Antibody-Conjugated Drug-Coated MENPs (AC-DC-MENPs) 602; applying, ingesting or injecting a solution containing AC-DC-MENPs to an area or intravenously into the blood stream and allowing the AC-DC-MENPs to bind to the targeted bacteria or viruses 603; and applying a magnetic field to cause the AC-DC-MENPs to release the drug or chemical to interrupt the function or kill the targeted bacteria or viruses 604, as shown in FIG. 6. The magnetic field for releasing the chemical or drug can be constant as produced by one or more permanent magnets, or alternating as produced by electromagnets driven by varying electric currents under the control of a microcontroller or other analog or digital control circuits.

In one embodiment, AC-MENPs or AC-DC-MENPs is used topically for killing bacteria or viruses on the surface of skins or in skin pores, e.g., in treating bacterial acne. A solution of AC-MENPs or AC-DC-MENPs is applied to the affected skin area, and a DC magnetic field, or a DC and an AC magnetic field is applied to kill the bacteria or viruses using the induced electric field and/or the release chemical or drug.

Although the foregoing descriptions of the preferred embodiments of the present inventions have shown, described, or illustrated the fundamental novel features or principles of the inventions, it is understood that various omissions, substitutions, and changes in the form of the detail of the methods, elements or apparatuses as illustrated, as well as the uses thereof, may be made by those skilled in the art without departing from the spirit of the present inventions. Hence, the scope of the present inventions should not be limited to the foregoing descriptions. Rather, the principles of the inventions may be applied to a wide range of methods, systems, and apparatuses, to achieve the advantages described herein and to achieve other advantages or to satisfy other objectives as well.

I claim:

1. A method for targeting cells that are less negatively charged than surrounding cells comprising
    injecting a solution of nano-particles at an area, wherein the nano-particles are Magneto-Electric Nano-Particles (MENPs),
    increasing negative charges of the nano-particles so as to produce an electric gradient field, which is accomplished by applying for a period of time an external field on the MENPs; and
    the electric gradient field pushing or driving the nano-particles from the area toward the less negatively charged cells;
    wherein the method further comprises (1) placing, injecting or implanting one or more permanent magnets or electro-magnets in a cancer site, wherein the magnets) serves to attract MENPs to and increase accumulation of MENPs in the cancer site, as well as to increase the negative charges of the MENPs to steer the MENPs towards cancer cells; (2) injecting or implanting wires, liquid capsules, injectable macro-particles, made of permanent magnetic material into a solid tumor site that is inside a body or an organ, wherein the magnetic field produced by these injected or implanted magnetic sources serve to localize and accumulate the MENPs at cancer sites, and at the same time to enhance the electric field gradient to push MENPs to cancer cells; or (3) using an apparatus formed into a shape and dimension to fit a target area or volume that is made of or using permanent magnetic material and with one or more electromagnets embedded in the apparatus to generate a constant magnetic field and a changing magnetic field simultaneously.

2. The method in claim 1 wherein the MENPs are made with a basic structure of $CoFe_2O_4$—$BaTiO_3$ coreshell.

3. The method in claim 2 wherein the nano-particles are further surface functionalized by a compound.

4. The method in claim 1 further comprising
    using an external field to guide and/or enhance an accumulation of the nano-particles into a site containing the less negatively charged cells than the surrounding more negatively charged cells.

5. The method in claim 2 wherein the external field comprises a magnetic field that is a changing field generating a varying or pulsating force to push MENPs towards less negatively charged cells.

6. The method in claim 5 wherein the changing magnetic field is generated by driving a periodic or irregular alternating current through one or more electro-magnets, or by varying position of one or more permanent magnets.

7. The method in claim 6 further comprising changing period, pattern, magnitude and/or direction of an alternating magnetic field to achieve desired movements of the MENPs.

8. The method in claim 1, wherein the increasing of the negative charges of the nano-particles is accomplished by using nano-particles that are made of a chemical composition that produces a negative surface charge or are coated or conjugated with molecules that increase the negative surface charge when they are in a blood stream or body fluid.

* * * * *